United States Patent
Ohki et al.

(10) Patent No.: US 11,674,941 B2
(45) Date of Patent: Jun. 13, 2023

(54) WATER BALANCE SENSOR STATION SYSTEMS

(71) Applicant: METER Group, Inc., Pullman, WA (US)

(72) Inventors: Takuya Ohki, Pullman, WA (US); Zach Campbell, Pullman, WA (US); Scott H. Campbell, Pullman, WA (US); Gaylon S. Campbell, Pullman, WA (US)

(73) Assignee: METER Group, Inc., Logan, UT (US)

( * ) Notice: Subject to any disclaimer, the term of this patent is extended or adjusted under 35 U.S.C. 154(b) by 0 days.

(21) Appl. No.: 17/568,378

(22) Filed: Jan. 4, 2022

(65) Prior Publication Data
US 2022/0128537 A1   Apr. 28, 2022

Related U.S. Application Data

(63) Continuation of application No. 16/396,278, filed on Apr. 26, 2019, now Pat. No. 11,215,598.

(51) Int. Cl.
*G01N 33/12* (2006.01)
*A23L 5/10* (2016.01)
(Continued)

(52) U.S. Cl.
CPC ............ *G01N 33/12* (2013.01); *A23B 4/044* (2013.01); *A23L 5/15* (2016.08); *G01G 23/36* (2013.01);
(Continued)

(58) Field of Classification Search
CPC ........ G01N 33/12; G01N 27/041; A23L 5/15; A23L 13/00; A23B 4/044; G01G 23/36; G01K 1/026; A23Y 2002/00
See application file for complete search history.

(56) References Cited

U.S. PATENT DOCUMENTS 4,876,426 A * 10/1989 Smith ................ A21B 1/48
219/684
5,069,273 A   12/1991 Ohearne
(Continued)

FOREIGN PATENT DOCUMENTS

AU   2003302713 A1 *  7/2004  ............... A21B 3/04
CH     663472 A5    12/1987
(Continued)

OTHER PUBLICATIONS

Bluetooth SIG Proprietary (Jan. 21, 2019) Bluetooth Core Specification v5.1. Retrieved from: https://www.bluetooth.com/specifications/bluetooth-core-specification.

*Primary Examiner* — Gail Kaplan Verbitsky
(74) *Attorney, Agent, or Firm* — Dorsey & Whitney LLP (57) ABSTRACT

Sensor stations and related systems and methods to monitor and measure properties of food products in food processing structures such as cure rooms, smokehouses, ovens, and related structures. The sensor stations allow real-time, local collection of product properties and their surrounding environmental conditions in order to improve efficiency, reduce product waste and guesswork, and to provide data-based analysis for decision making. Sensor stations can be mounted to food supports and can be in electronic communication with each other and with intermediate nodes that provide a connection to other external computing devices that provide analysis and alerts to users and technicians. Various non-destructive modeling systems for determining water activity and pH of changing products are also provided.

20 Claims, 5 Drawing Sheets

(51) Int. Cl.
*A23B 4/044* (2006.01)
*G01G 23/36* (2006.01)
*G01K 1/02* (2021.01)
*G01N 27/04* (2006.01)
*A23L 13/00* (2016.01)

(52) U.S. Cl.
CPC ........... *G01K 1/026* (2013.01); *G01N 27/041* (2013.01); *A23L 13/00* (2016.08); *A23V 2002/00* (2013.01)

(56) References Cited

U.S. PATENT DOCUMENTS

| | | |
|---|---|---|
| 5,479,104 A | 12/1995 | Cambell |
| 6,080,972 A | 6/2000 | May |
| 6,904,789 B2 | 6/2005 | Campbell et al. |
| 8,387,518 B2 | 3/2013 | Carpenter et al. |
| 8,723,167 B2 | 5/2014 | Sato et al. |
| 8,877,274 B2 | 11/2014 | Bell |
| 9,857,234 B2 | 1/2018 | Schechter et al. |
| 10,653,170 B1 | 5/2020 | Micka |
| 2004/0022298 A1 | 2/2004 | Gunawardena et al. |
| 2008/0233250 A1 | 9/2008 | Sastry et al. |
| 2009/0205512 A1 | 8/2009 | Carpenter et al. |
| 2014/0170275 A1 | 6/2014 | Bordin |
| 2014/0272046 A1 | 9/2014 | Micka et al. |
| 2015/0010679 A1 | 1/2015 | Strong et al. |
| 2015/0226683 A1 | 8/2015 | Feldman et al. |
| 2017/0051945 A1 | 2/2017 | Micka et al. |
| 2018/0066996 A1 | 3/2018 | Schechter et al. |
| 2018/0206536 A1 | 7/2018 | Kelleher et al. |
| 2019/0004353 A1 | 1/2019 | Campbell |
| 2019/0269142 A1 | 9/2019 | Lagares Corominas |
| 2020/0120958 A1 | 4/2020 | Wu et al. |
| 2020/0139554 A1 | 5/2020 | Sinnet et al. |
| 2020/0170447 A1 | 6/2020 | Büttner et al. |
| 2020/0200744 A1 | 6/2020 | Yasovsky |
| 2020/0267996 A1 | 8/2020 | Stork Genannt Wersborg et al. |
| 2020/0278117 A1 | 9/2020 | Bhogal |
| 2020/0370846 A1 | 11/2020 | Chien |
| 2021/0037841 A1 | 2/2021 | Bozzato et al. |
| 2021/0235906 A1 | 8/2021 | Skartland |

FOREIGN PATENT DOCUMENTS

| | | | |
|---|---|---|---|
| CN | 101629857 A * | 1/2010 | |
| DE | 3422313 A1 | 12/1985 | |
| JP | 359116022 A | 7/1984 | |
| JP | S635647 B2 * | 2/1988 | |
| JP | H8135979 A * | 5/1996 | |
| JP | 2004194509 A * | 7/2004 | |
| JP | 3706475 B2 * | 10/2005 | ............ F23K 5/08 |
| KR | 100295270 B1 * | 9/2001 | |
| KR | 100623868 B1 * | 9/2006 | |
| RU | 2442426 C1 | 2/2012 | |
| WO | WO9110388 A1 * | 7/1991 | |
| WO | 2008023370 A2 | 2/2008 | |
| WO | 2013139912 A1 | 9/2013 | |
| WO | WO-2017067671 A1 * | 4/2017 | ............ F24C 15/003 |

\* cited by examiner

WATER BALANCE SENSOR STATION SYSTEMS

RELATED APPLICATION

This is a continuation of U.S. patent application Ser. No. 16/396,278, filed on 26 Apr. 2019, now pending, the disclosure of which is incorporated, in its entirety, by this reference.

TECHNICAL FIELD

The present disclosure generally relates to sensors and systems for monitoring food processing and more specifically relates to remote monitoring systems and methods for modeling the status of curing, drying, smoking, and otherwise processing meat-based food products.

BACKGROUND

In the field of food processing, batch smoking and curing processes are often uncontrolled and managed by less-than-precise methods and equipment. Millions of dollars in product is wasted through destructive testing, improper control of processes, reworking, and scrap. Current processes for monitoring and managing batch curing and drying processes are very limited and consist of significant manual labor and uncertainty.

Generally, a technician is required to manually pull samples and destructively test the product to collect data on moisture content, pH, and water activity. Temperatures in drying and curing chambers are typically set to constant temperatures that are potentially adjusted based on a technician's previous experience. Using this information, previous experience, and a degree of trial and error, the technician determines when the product is ready and then removes the product. This process has many inherent shortcomings. Products such as jerky and other meats are relatively high in terms of cost, so destructive testing is expensive. Also, this process has difficulty monitoring fermentation and drying, leading to an overly-frequent need for extensive reworking and scrapping.

The current methodology for monitoring pH is done by using a traditional pH electrode. Samples are manually removed from the cure and smokehouse, which in certain cases can require adjusting the temperature. Depending on the methodology and the probe type, sample homogenization and extraction may be necessary. Similarly, any moisture content or water activity readings can require similar homogenization and destructive testing. While these steps are necessary to validate the process, they do not always properly capture the curing and drying processes. Accordingly, there is a constant need for improvements to food processing techniques and equipment.

SUMMARY

One aspect of the present disclosure relates to a sensor station comprising a housing, a computing device positioned in the housing, and a set of sensors in electrical communication with the computing device. The set of sensors can include a load cell to measure a weight of a food product, a relative humidity sensor to measure ambient relative humidity around the food product, a first temperature sensor to measure a food temperature of the food product, and a second temperature sensor to measure an ambient temperature around the food product. The sensor station can also have an electronic communications interface connected to the computing device, with the electronic communications interface being configured to transmit electronic signals from the computing device to an external device.

In some embodiments, the sensor station further comprises a mount to hang the housing from a support surface, wherein the load cell is positioned in the housing and connected to a food support member extending from a lower surface of the housing, with the food support member being configured to hold the weight of the food product. The first temperature sensor can also comprise a probe configured to contact the food product.

The set of sensors further can further comprise a pH sensor to measure pH of the food product or a water activity sensor to measure water activity of the food product. A food support member can also be included which extends from an external surface of the housing and is configured to hold the weight of the food product. A mobile food platform can also be included, wherein the housing is mounted to the mobile food platform. The electronic communications interface can comprise a wireless transceiver connected to the computing device, wherein the computing device is configured to receive measured data from a second sensor station via the wireless transceiver and to store and transmit the measured data. The electronic signals can comprise a water activity value of the food product.

In some embodiments, the set of sensors further comprises a dielectric permittivity sensor to measure dielectric permittivity of the food product and an electrical conductivity sensor to measure electrical conductivity of the food product. The electronic signals can comprise a pH of the food product and a water content of the food product based on the dielectric permittivity of the food product and the electrical conductivity of the food product.

The sensor station can also comprise a storage structure, and the housing can be positioned in the storage structure. A third temperature sensor and a second relative humidity sensor can be included, wherein the storage structure comprises an air inlet and an air outlet, the second temperature sensor is configured to measure a first ambient temperature at the air inlet, the relative humidity sensor is configured to measure a first relative humidity at the air inlet, the third temperature sensor is configured to measure a second ambient temperature at the air outlet, and the second relative humidity sensor is configured to measure a second relative humidity at the air outlet.

Another aspect of the disclosure relates to a food processing method, comprising receiving set of sensor measurements from a set of sensors, with the set of sensors being positioned in a food processing structure, tracking a water activity value over time of a food product in the food processing structure based on the sensor measurements, determining that the food product is ready for removal from the food processing structure based on the water activity value reaching a threshold amount, and providing an alert to remove the product from the food processing structure.

In some configurations of the method, the set of sensor measurements can comprise a temperature of the food product, a dry bulb temperature, and a relative humidity. The set of sensor measurements can also comprise a temperature of the food product and a weight of the food product, or an electrical permittivity of the food product and an electrical conductivity of the food product. The set of sensor measurements can comprise an inflow temperature at an inflow location of the food processing structure, an inflow relative humidity at the inflow location, an outflow temperature at an outflow location of the food processing structure, and an outflow relative humidity at the outflow location.

In another aspect of the disclosure a food processing station is provided that can comprise a housing having an internal chamber, a set of sensors positioned in the internal chamber, a computing device connected to the set of sensors and configured to receive signals from the set of sensors, with the computing device having a processor configured to execute electronic instructions. The electronic instructions can be instructions to determine a water activity value of a food product in the internal chamber based on the signals from the set of sensors and transmit a signal indicating the water activity value of the food product.

The housing can be part of an oven, a smokehouse, or a cure room. The set of sensors can comprise at least two thermometers and at least one of a relative humidity sensor and a weight sensor. The set of sensors can comprise comprises a pH sensor.

The above summary of the present invention is not intended to describe each embodiment or every implementation of the present invention. The Figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

The present disclosure relates to systems and methods for tracking food properties as they dry, cure, or undergo similar changes in their temperature, pH, water activity, or water content. Embodiments of the present disclosure can help to gather real-time data relating to these properties and can then use predictive physical models to suggest proper cure times, mitigate losses, human error, and guesswork, and provide food makers with improved awareness of the status of their products while they are manufactured.

One aspect of the disclosure relates to devices such as sensor stations for remotely monitoring key food processing parameters. The sensor stations can be deployed in a multitude of different types of food processing locations and environments and can be especially beneficial for managing and monitoring foods undergoing curing and smoking processes. In some embodiments, the sensor stations can be interlinked via wired or wireless connections to a local node located in a food processing station or structure such as an oven, smokehouse, or cure room. In some embodiments, the sensor stations can be distributed throughout the structure and can be configured to mount to a cart, tray, shelf system, or other product-supporting apparatus. Multiple sensor stations can be positioned in each food processing structure and can communicate wirelessly with each other or with external devices using a mesh- or star-based low energy wireless topology such as, for example, BLUETOOTH® Low Energy (BLE), BLUETOOTH® mesh, or other wireless protocols.

A sensor station can be an intermediate data collection and transfer apparatus between sensors and an external network device such as, for example, an external computer, server, Internet-connected database, user device, or similar device. The intermediate data collection and transfer apparatus can be connected by a wired connection to a network (e.g., a local area network (LAN)) of the food processing factory or plant at which the food product is produced. A device can collect process data that is made available through internal programmable logic controller (PLC) networks and aggregate it with data collected by the sensor nodes of connected sensor stations. Data can be streamed or transmitted at spaced-apart intervals or in real-time to an external network device for constant monitoring. If a network connection is lost, the intermediate apparatus can collect and aggregate data for an extended time period (e.g., many days) and can transmit the data to an external network device once a connection to the network is restored. In some embodiments, the external network device can provide information to user devices such as a computer, phone, tablet, or similar device of a technician or factory operator to allow the user to monitor food parameters in real time.

A sensor station of the present disclosure can comprise a set of sensors such as, for example, a temperature sensor, a relative humidity sensor, a weight or force sensor, a moisture content sensor, an electrical conductivity sensor, and a water activity sensor. A sensor can be used to determine the temperature of a sample portion of the food product being monitored. A food product temperature (i.e., a sample temperature) can be used to perform a kill step in both processed and unprocessed meats. In other words, the temperature of a sample of the food product can be used to monitor whether threshold temperatures are reached or exceeded in order to eliminate harmful contaminants such as microbes. For example, the food product can be raised to a temperature greater than or equal to 50 degrees Celsius for a predetermined period of time to reduce the risk of these unwanted substances.

The temperature of the food product, whether on its surface or an internal temperature, can also beneficially be used to monitor the status of a drying food product. The surface and internal temperatures can be measured using temperature sensors such as thermocouples or thermistors deployed in or on the sample. Surface temperatures can also be measured remotely using an infrared (IR) thermopile, thermal imaging, and similar devices and techniques.

Sensors can also be configured to determine an ambient chamber temperature. This temperature can be a dry bulb temperature of air in a chamber in which the food product is being heated, smoked, cured, dried, or otherwise modified. A chamber temperature can be actively collected and aggregated with other sensor node data.

Some sensor stations can also comprise relative humidity (RH) sensors to measure influent and effluent RH of a chamber in which the food product is processed. For example, a drying room can be treated as control volume with a single inflow location and a single outflow location. By monitoring the RH and temperature of both the influent and effluent portions of the chamber, the system can calculate a total moisture gained or lost in the chamber over time. This information can then be used to model the drying or curing process with improved accuracy. Thus, RH sensors can be positioned to measure RH at both influent and effluent locations in the chamber, and the RH changes can be monitored over time.

In some embodiments, a weight or force sensor such as a load cell can also be employed to improve food parameter modeling. A load cell mounted to a drying rack or to a sensor station bearing the weight of a food product can be used to track weight changes in the product (e.g., due to water loss) as the product dries or otherwise changes. The water loss can accordingly be correlated with other properties of the product or chamber such as dryness, temperature, weight, etc. without needing to destructively test or move the product.

A sensor station can also comprise moisture content sensors and electrical conductivity sensors. In some embodiments, a single probe or sensor device can provide multiple measurements of one or more different kinds. A dielectric sensor such as, for example, the electrical sensor in U.S. Pat. No. 5,479,104 to Campbell (the contents and disclosure of which is hereby incorporated by reference in its entirety) can be used to measure dielectric permittivity of a sample and can therefore be used to determine moisture content by inference. Moisture content can be a primary indicator of a drying process and can also be valuable in curing processes, so such sensors can provide valuable information when determining the status of a food product undergoing changes such as fermentation and smoking.

Lacto-fermentation can change the properties of food products such as meats. During this process, sugars can be converted to lactic acid, thereby causing in a drop in the pH of a product sample. A pH electrode can be used to track the pH of a product with sufficient sample preparation. In some configurations, the acidification of a sample can affect its electrical conductivity. This change, when monitored, can be used to infer pH and the overall fermentation reaction. Thus, a dielectric sensor or other electrical conductivity sensor can be used to determine pH and fermentation properties of a food product.

A water activity sensor can also be employed with a sensor station to determine water activity of a food product. Water activity is intrinsically linked to many quality characteristics such as microbial growth, so precise monitoring and control of this parameter can be used to optimize drying and curing processes.

A typical smokehouse facility can have multiple stand-alone smoke rooms or other chamber structures where the product is placed on drying racks, hooks, shelves, or other supports. In drying and smoking applications, the status of a meat food product can be characterized by measuring the product temperature, the product weight loss, the product water activity, and the temperature of the smoking room. This information can be used to model the process, and, accordingly, steps completed in the process such as completion of a kill step or reaching a time to remove the product from the food processing structure. Moisture content can also be tracked by monitoring the effluent and influent gas streams of the structure.

Figure 1:
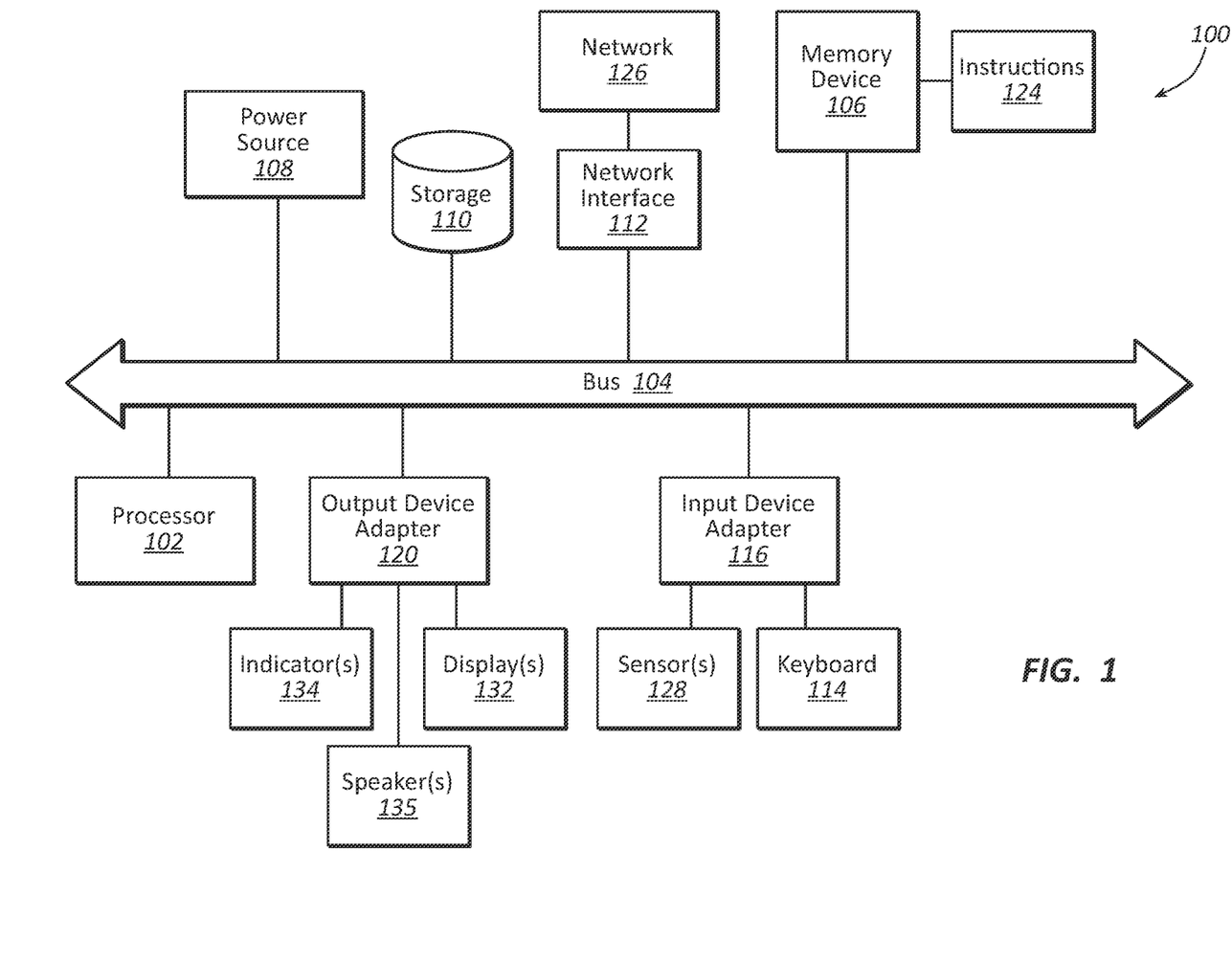
FIG. 1 shows a high-level block diagram of a computer system.

Additional details, features, and embodiments will be provided in connection with the figures. FIG. 1 shows a high-level block diagram of a computer system 100 for embodiments of the present disclosure. In various embodiments, the computer system 100 can comprise various sets and subsets of the components shown in FIG. 1. Thus, FIG. 1 shows a variety of components that can be included in various combinations and subsets based on the operations and functions performed by the system 100 in different embodiments. It is noted that, when described or recited herein, the use of the articles such as "a" or "an" is not considered to be limiting to only one, but instead is intended to mean one or more unless otherwise specifically noted herein.

The computer system 100 can comprise a central processing unit (CPU) or processor 102 connected via a bus 104 for electrical communication to a memory device 106, a power source 108, an electronic storage device 110, a network interface 112, an input device adapter 116, and an output device adapter 120. For example, one or more of these components can be connected to each other via a substrate (e.g., a printed circuit board or other substrate) supporting the bus 104 and other electrical connectors providing electrical communication between the components. The bus 104 can comprise a communication mechanism for communicating information between parts of the system 100.

The processor 102 can be a microprocessor or similar device configured to receive and execute a set of instructions 124 stored by the memory 106. The memory 106 can be referred to as main memory, such as random access memory (RAM) or another dynamic electronic storage device for storing information and instructions to be executed by the processor 102. The memory 106 can also be used for storing temporary variables or other intermediate information during execution of instructions executed by the processor 102. The storage device 110 can comprise read-only memory (ROM) or another type of static storage device coupled to the bus 104 for storing static or long-term (i.e., non-dynamic) information and instructions for the processor 102. For example, the storage device 110 can comprise a magnetic or optical disk (e.g., hard disk drive (HDD)), solid state memory (e.g., a solid state disk (SSD)), or a comparable device. The power source 108 can comprise a power supply capable of providing power to the processor 102 and other components connected to the bus 104, such as a connection to an electrical utility grid or a battery system.

The instructions 124 can comprise information for executing processes and methods using components of the system 100. Such processes and methods can include, for example, the methods described in connection with FIG. 6. In some embodiments, the instructions 124 are stored by and performed by an external computing device (e.g., a device connected to the system 100 via the network interface 112).

The network interface 112 can comprise an adapter for connecting the system 100 to an external device via a wired or wireless connection. For example, the network interface 112 can provide a connection to a computer network 126 such as a cellular network, the Internet, a local area network (LAN), a separate device capable of wireless communication with the network interface 112, other external devices or network locations, and combinations thereof. In one example embodiment, the network interface 112 is a wireless networking adapter configured to connect via WI-FI®, BLUETOOTH®, BLE, Bluetooth mesh, or a related wireless communications protocol to another device having interface capability using the same protocol. In some embodiments, a network device or set of network devices in the network 126 can be considered part of the system 100. In some cases, a network device can be considered connected to, but not a part of, the system 100.

The input device adapter 116 can be configured to provide the system 100 with connectivity to various input devices such as, for example, a keyboard 114, one or more sensors 128, related devices, and combinations thereof. In an example embodiment, the input device adapter 116 is connected to a set of sensors including a thermometer, a pH sensor, a dielectric permittivity sensor, an RH sensor, a water activity sensor, and a force sensor. Thus, the sensors 128 can be used to transduce various properties of food products and their surroundings. The keyboard 114 or another input device (e.g., a mouse, buttons, or switches) can be used to provide user input such as input regarding the settings of the system 100.

The output device adapter 120 can be configured to provide the system 100 with the ability to output information to a user, such as by providing visual output using one or more displays 132 or indicators 134 or by providing audible output using one or more speakers 135. Other output devices can also be used. The processor 102 can be configured to control the output device adapter 120 to provide information to a user via the output devices connected to the adapter 120.

Figure 2:
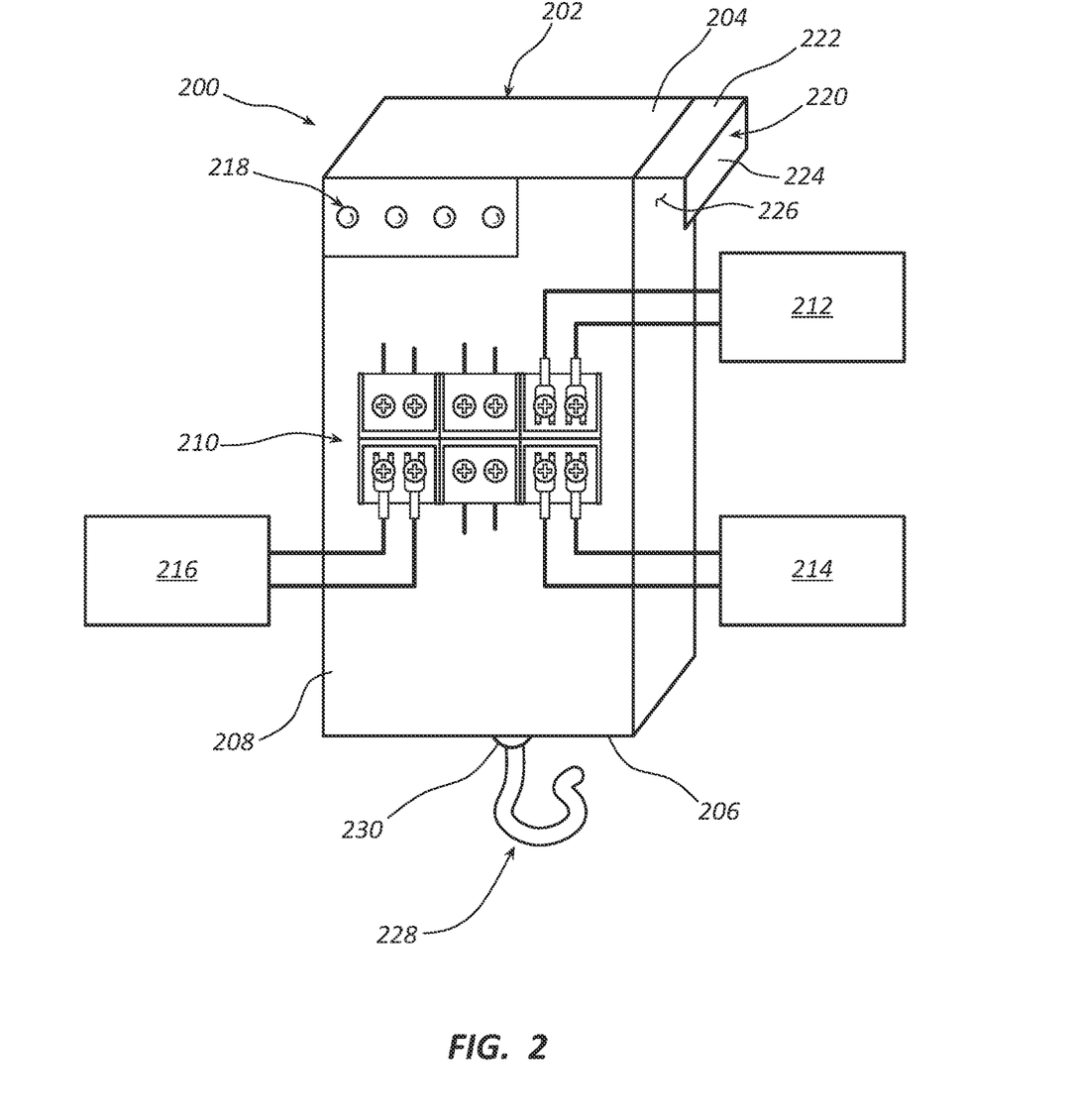
FIG. 2 is a diagrammatic view of a sensor station.

The system 100 can be a computing device configured to be implemented as part of a sensor station 200. FIG. 2 is a diagrammatic view of a sensor station 200 that can contain electronic components of the system 100 of FIG. 1 in a housing 202. The housing 202 can comprise a top end 204 and a bottom end 206. Lateral sides 208 of the housing 202 can extend between the top and bottom ends 204, 206. A computing device (e.g., components of the system 100) can be positioned within the housing 202 and can beneficially thereby be protected from damage caused by exposure to moisture, heat, and other ambient conditions in a smokehouse, cure room, oven, or similar food processing structure.

The input device adapter 116 can comprise a connection to an electrical interface 210 at a surface of the housing 202. The electrical interface 210 of FIG. 2 is shown as a screw terminal interface, but other electrical connection interfaces known in the art can be used in place of the screw terminal interface. The electrical interface 210 can provide an electrical connection to a set of sensors 212, 214, 216 positioned external to the housing 202. In some embodiments, the electrical interface 210 can be used to connect the station 200 to another sensor station, an antenna, an external power source, or other electrical components needed for the station 200 to function.

The output device adapter 120 of the system 100 can be connected to a display system or indicator system 218 of the sensor station 200. The indicator system 218 can comprise output devices such as lights or speakers to indicate to a user the status of the system and measurements made by sensors of the sensor station 200. For example, lights may be used to indicate a status of a food product being monitored, battery status (e.g., for a battery that is part of the power source 108), a wireless connection status, and other characteristics of the system 100 or station 200.

The station 200 can include a mount 220 to mount the housing to, or hang the housing from, a support surface. The mount 220 can comprise a hook-like member, an opening in a side of the housing 202 (e.g., an aperture to receive a protruding nail, hook, or similar structure), or related structure configured to receive a bar or cantilever structure on a wall, rack, shelf, or other surface of a food processing structure. For example, the station 200 can comprise a mount 220 having a horizontal portion 222 and a vertical portion 224 that define an internal cavity or reception area 226 within which a surface of a support structure can be positioned to suspend the station 200 from an elevated position.

The station 200 can also include a food support member 228 attached to a force sensor 230. The food support member 228 can comprise a hook, eyelet, handle, shelf, or similar structure configured to support the weight of a sample of a food product. For example, the food support member 228 can support links of a sausage draped over it. In some embodiments, the food support member 228 can penetrate or pierce the food product (e.g., a piece of jerky meat) to support the weight of the sample. Accordingly, the food support member 228 can comprise a sharpened or pointed tip.

The force sensor 230 can be a weight sensor such as a load cell or a strain gauge configured to transduce a force applied to the food support member 228. In some embodiments, the force sensor 230 is configured to transduce a downward-oriented force associated with the weight of a food product. The force sensor 230 can be positioned in the housing 202 or can be positioned at a surface of the housing at the bottom end 206. In some embodiments, the load cell can be connected to the mount 220. Thus, the weight of the food product at the food support member 228 can be transduced as a change in weight of substantially the entire station 200 when the food product is supported by the station 200. Accordingly, the station 200 can support the food product and sense its weight as it cures, dries, or otherwise changes. In some embodiments, the weight of the food product is closely associated with the water content of the food product, so the moisture in the food product can be inferred based in part on the output of the force sensor 230.

The set of sensors 212, 214, 216 can comprise a variety of transducers configured to sense properties of a sample food product or its environment. In various embodiments, the sensors 212, 214, 216 can comprise an external load cell, a relative humidity sensor to measure ambient relative humidity around the food product, a temperature sensor to measure a food temperature of a food product (e.g., a temperature probe to contact, to be mounted to, or to penetrate the food product), a temperature sensor to measure an ambient temperature around the food product (e.g., a thermocouple for measuring a dry bulb temperature of the air surrounding the food product), a pH sensor, a dielectric permittivity sensor, a water activity sensor, other sensors disclosed herein, similar sensors, multiples of these sensors, and combinations thereof. Different sensor combinations may be implemented at the electrical interface 210 for different types of food products, food processing techniques, food processing structures, or usage times.

In an example embodiment, a sensor station 200 configured to operate in a smokehouse can comprise a set of temperature sensors to measure product temperature, smoke room temperature, influent and effluent temperature of the smokehouse, and external ambient temperature. It can also include a load cell to monitor weight loss of a product in real-time so that the real-time moisture content of the product can be determined over time based on an initial moisture content value. A smokehouse sensor station can also include a water activity measurement device to monitor the water activity of the product and a dielectric sensor used to measure the complex permittivity of the product as it dries in order to predict the volumetric water content in situ.

In another example embodiment, a sensor station 200 can be configured to operate in a cure room, wherein water activity and pH are determined as controlling factors. Water activity can be monitored to limit or prevent microbial growth, and pH can be used to monitor the fermentation process by measuring a decrease in pH due to lactic acid formation in a food product. The station 200 can include sensors comprising a dielectric sensor for measuring the complex permittivity of the product which correlates with the moisture content of the product. Thus can further reinforce water activity models and can be used to optimize yields. The sensors can also include a pH sensor, a water activity sensor or probe, and a temperature sensor.

Figure 3:
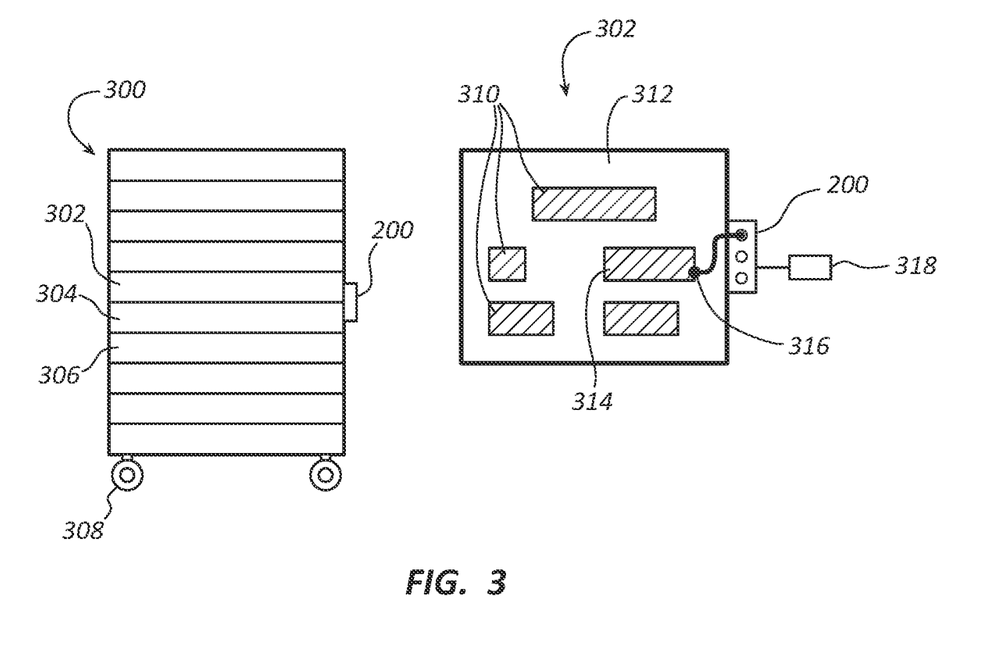
FIG. 3 is a diagrammatic side view of a mobile food platform and a top view of a food support shelf.

FIG. 3 is a diagrammatic side view of a mobile food platform 300 and a top view of a food support shelf 302 according to embodiments of the present disclosure. The mobile food platform 300 can comprise a set of food support shelves 302, 304, 306, etc. that are mounted to each other on a movable rack having wheels 308 and supports that hold the shelves together. The mobile food platform 300 can therefore be easily moved into and out of a food processing structure such as an oven or cure room. The mobile food platform 300 can also comprise at least one sensor station 200 mounted to or otherwise supported by a shelf (e.g., 302) or by other structures of the mobile food platform 300 (e.g., beams holding up the shelves). The sensor station 200 can be configured with high mobility by comprising a mobile power source (e.g., a battery, fuel cell, or portable generator) and a wireless communications interface (e.g., an antenna) so that the mobile food platform 300 can be easily moved without damaging cords or other portions of the sensor station 200. The sensor station 200 can be mounted to the mobile food platform 300 using the mount 220, such as by being hooked over a bar extending across a shelf or by extending through a hole in a shelf. In some embodiments, the sensor station 200 can simply rest on a shelf or similar support.

The top view of the example shelf 302 is shown on the right side of FIG. 3 with a set of food products 310 spread across its upward-facing support surface 312. A tested food product sample 314 can be connected to at least one probe 316 connected to the sensor station 200. The at least one probe 316 can provide measurements of properties of the product sample 314 such as its pH, temperature, dielectric permittivity, and other properties described herein. The sensor station 200 can also comprise external probes 318 connected to the mobile food platform 300, other shelves (e.g., 304, 306), other product samples (e.g., on other shelves 304, 306), or otherwise extending from the sensor station 200. For example, an external probe 318 can be used to measure relative humidity around the mobile food platform 300 such as an Ambicina probe.

In some embodiments, at least one shelf 302 can be removable from the mobile food platform 300 and can therefore be portable relative to the other shelves 304, 306. The sensor station 200 can move with the at least one shelf 302 and can thereby remain connected to the product sample 314 to provide consistent measurements of the sample 314 as it is moved.

Figure 4:
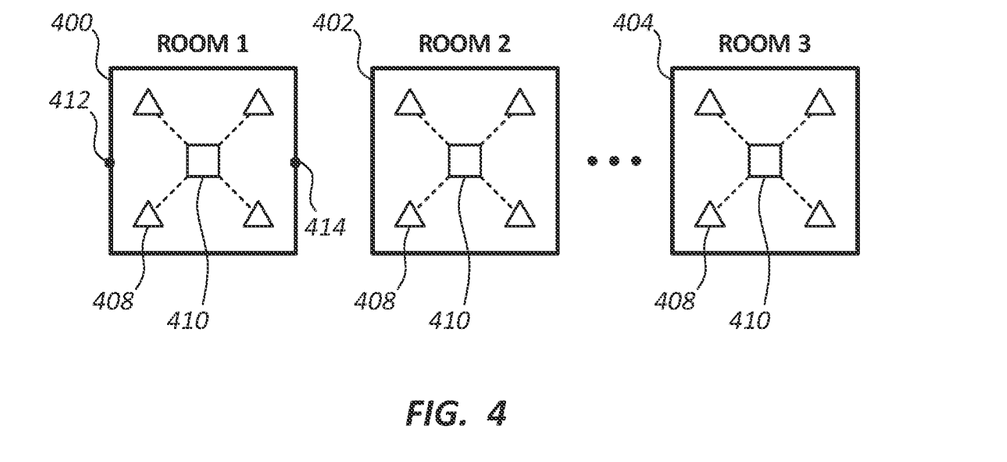
FIG. 4 is a diagram of a set of rooms configured to contain multiple sensor stations and intermediate nodes.

FIG. 4 is a diagram of a set of rooms 400, 402, 404 configured to contain multiple sensor stations 408 (depicted as triangles) and intermediate nodes 410 (depicted as the central squares). The rooms 400, 402, 404 can be smokehouses, cure rooms, ovens, or other areas in a factory or other facility. The rooms can be referred to as storage structures. Although three rooms are shown in FIG. 4, it will be understood that any number of rooms can be used.

In some embodiments, the rooms 400, 402, 404 comprise large amounts of material that can interfere with the transmission of wireless signals, such as large metal panels, walls, shelves, etc. Accordingly, the sensor stations 408 and intermediate nodes 410 can be configured to mitigate the effects of the interference. In some embodiments, the respective sensor stations 408 within each room 400, 402, 404 are in electrical communication with their respective intermediate node 410, and the intermediate node 410 can be configured to gather and retain the sensor data sent by the sensor stations 408. The sensor stations 408 can be in wireless electronic communication with the intermediate node 410.

In some configurations, the wireless connection between a sensor station 408 and the intermediate node 410 can be a low-power or low-range connection, wherein the wireless signal produced by the sensor station 408 does not significantly penetrate through the walls of the room 400 in which it is located. In other words, the wireless signal of the sensor stations 408 can be significantly attenuated by the material of the room 400 surrounding the sensor stations 408. Accordingly, the intermediate node 410 can connect to the sensor stations 408 within the same room (e.g., 400) in which it is located, but it cannot directly connect to the sensor stations 408 in other rooms (e.g., 402, 404).

The intermediate node 410 can comprise an electronic storage medium for storing the sensor information transmitted by the sensor stations 408. The stored information can indicate the sensor station that sent the signal, the type of product it is monitoring, the type of room it is located in, the measurements made by the sensor station, the status of the sensor station, and related information. In some embodiments, the intermediate node 410 can comprise a wired or wireless electrical connection to an external network device (e.g., in network 126) to provide its stored information with at least one other computing device. See FIG. 5. In some embodiments, the intermediate node 410 is configured to store information from the sensor stations 408 even if a link to an external computing device is disabled. Reestablishing the connection between the intermediate node 410 and the external computing device can allow the accumulated data to be transferred away from the intermediate node 410. Accordingly, the intermediate node 410 can receive sensor information in real-time from the sensor stations 408 and can transfer that information to an external computing device in real-time. If the real-time link between the sensor stations 408, intermediate node 410, or external device is lost, intervening information can be stored and then sent once a connection is reestablished.

In some embodiments, the sensor stations 408 can be in electrical communication with each other within a room (e.g., 400) by a wired or wireless electronic communications interface. The intermediate node 410 can also be a sensor station. Some or all of the sensor stations can receive and store sensor information transmitted from the other sensor stations in their room.

Figure 5:
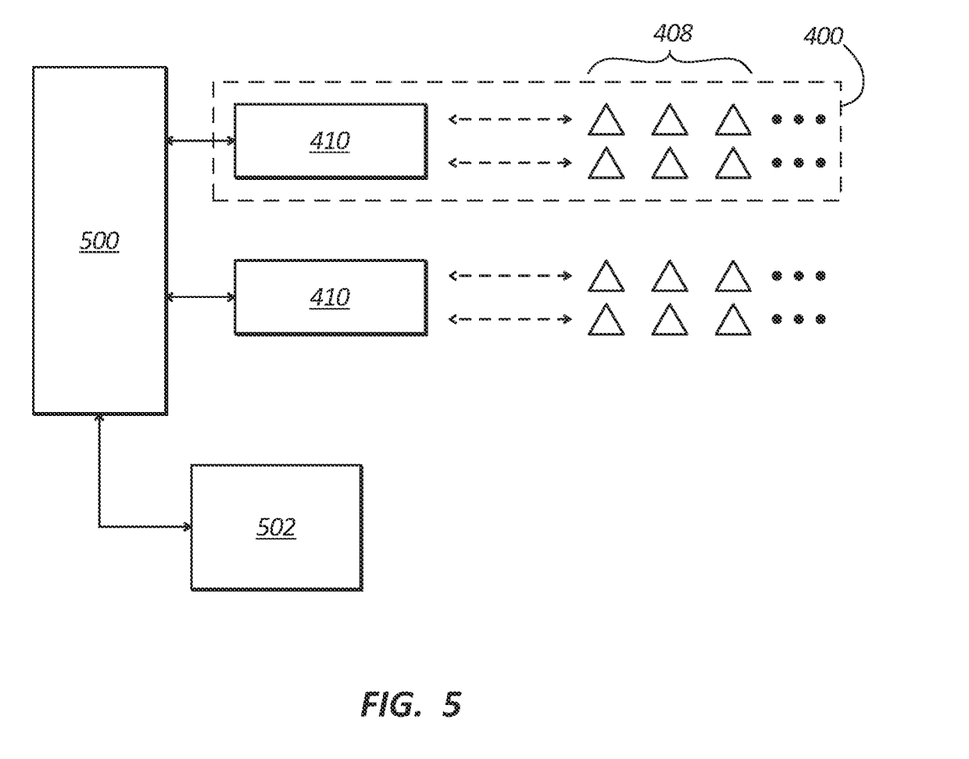
FIG. 5 is a diagram of a device network configuration.

FIG. 5 is another diagram of a device network configuration. The sensor stations 408 can be connected to the intermediate nodes 410 which are also connected to an external computing device 500. The external computing device 500 can be a control server or similar computer configured to centrally aggregate the data transferred from the sensor stations 408 and to provide information and alerts to a user. The information and alerts can be provided to a user device 502 that is in electronic communication with the external computing device 500.

The user device 502 can provide analytics, user prompts, alerts, sounds, visuals, and other information to the user that shows the status or progress of food products being monitored by the sensor stations 408. For example, the user device 502 can indicate to a user that it is time to remove a batch of product from a room 400 when, for example, calculated or measured water activity and pH values of the product reach desired thresholds. The network configuration of the sensor stations 408, intermediate nodes 410, and the external computing device 500 can be referred to as a wireless star topology or a wireless mesh topology.

Figure 6:
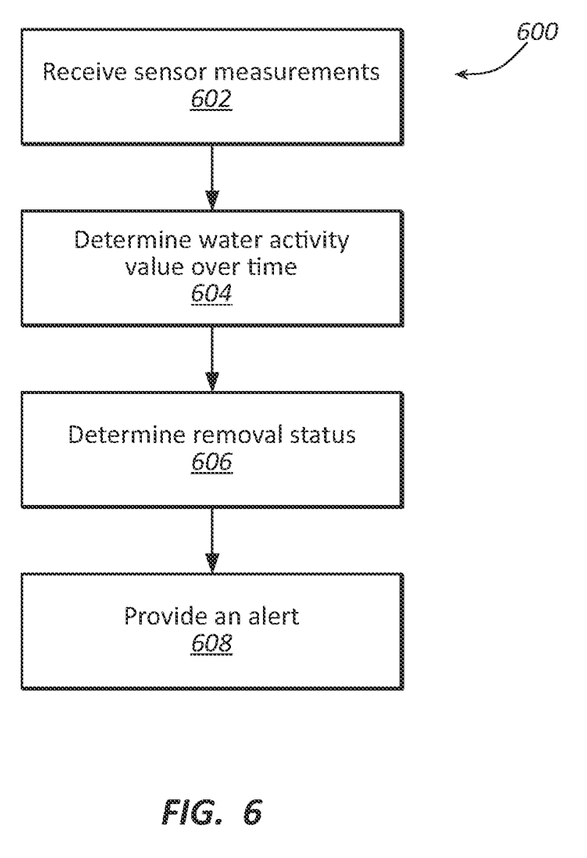
FIG. 6 is a diagram of a method of food processing that can be used with the systems and apparatuses of FIGS. 1-5.

FIG. 6 is a diagram of a method of food processing that can be used with the systems and apparatuses of FIGS. 1-5. In cases where water activity and/or pH of a product is not feasible, sensor data from the sensor stations described herein can be used to model those properties in real-time. A sensor station can collect data using multiple methods which can then be used by an external computing device 500 to develop a predicted water activity or other product parameter.

A wet bulb temperature is the temperature at which a thermocouple or other thermometer would read if covered with a saturated rag. This temperature will read below the dry bulb temperature due to the evaporation of water from the wet rag. The actual reading will be dependent upon the relative humidity and a dry bulb temperature. This value can be used in smokehouse environments to ensure that a kill step has been achieved. As a simplification, a dry bulb thermometer coupled with an RH sensor can be used to calculate the wet bulb temperature with accuracy.

Because the meat starts out in a saturated state (i.e., 1.0 $a_w$), with suitable evaporative transfer the product will reach an equilibrium temperature. Such a value agrees with the calculated and measured wet bulb temperature. As the product dries, the product temperature will remain at the wet bulb temperature until the water activity drops below 1.0. At this point, we can use the deviation between the product temperature and the ideal wet bulb to calculate the product water activity using first principles.

Accordingly, the method 600 can comprise receiving a set of sensor measurements from a set of sensors positioned in a food processing structure (as in block 602), tracking a water activity value over time of a food product in the food processing structure based on the sensor measurements (as in block 604), determining that the food product is ready for removal from the food processing structure based on the water activity value reaching a threshold amount (as in block 606), and providing an alert to remove the product from the food processing structure (as in block 608).

In various embodiments, the set of sensor measurements can comprise different properties and values. For example, the sensor measurements can comprise a temperature of the food product, a dry bulb temperature, and a relative humidity to calculate theoretical wet bulb temperature. In blocks 604 and 606, the wet bulb temperature can be correlated to the water activity, as explained above. In such an embodiment, the sensor station can use a VP4 sensor or similar device for measuring relative humidity and temperature.

In another embodiment, water activity can be determined based on moisture content using a product-specific calibration. In this case, the weight loss or weight gain of a sample of the product (as measured by a load cell) and a starting moisture content value can be used to calculate water activity of the product over time. The calculated water activity can be temperature-corrected based on measurements from a temperature sensor.

In another embodiment, a dielectric permittivity and electrical conductivity sensor can be employed to sense conductivity and permittivity of a sample in a manner correlated with the pH and water content of the sample. Accordingly, a dielectric permittivity and electrical conductivity sensor can be used to determine the water activity and pH over time. This can be especially useful in cure room applications where pH is an important factor to monitor in the fermentation process. The method 600 can further comprise determining pH over time in block 604, and the pH can be part of the characteristics monitored when determining a removal status in block 606.

In yet another embodiment, a water balance of the environment of the food processing structure can be calculated. A traditional smoke room or similar structure (e.g., room 400) can be treated as a sealed environment except for fixed airflow entrance and exit locations (e.g., entrance 412 and exit 414 in FIG. 4). Therefore, vapor density of the inflow and outflow air can be monitored to determine the amount of water lost during drying of the food product. By comparing this information to initial moisture content values of the food product, the moisture content of the food product can be determined in real-time. Thus, the sensor measurements can comprise an inflow temperature at an inflow location (e.g., 412) of the food processing structure (e.g., 400), an inflow relative humidity at the inflow location, an outflow temperature at an outflow location (e.g., 414) of the food processing structure, and an outflow relative humidity at the outflow location.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A sensor station system, comprising:
   at least one room having an air inlet and an air outlet;
   a computing device;
   a set of sensors in electrical communication with the computing device, the set of sensors including:
      an inlet relative humidity sensor to measure an inlet relative humidity at the air inlet of the at least one room;
      an inlet temperature sensor to measure an inlet temperature at the air inlet of the at least one room;
      an outlet relative humidity sensor to measure an outlet relative humidity at the air outlet of the at least one room; and an outlet temperature sensor to measure an outlet temperature at the air outlet of the at least one room;
wherein the computing device is configured to calculate a water balance of the at least one room based on the measured inlet relative humidity, the inlet temperature, the outlet relative humidity, and the outlet temperature of the at least one room over time.

2. The sensor station system of claim 1, wherein the computing device comprises a processor and a memory device in electronic communication with the processor, the memory including electronic instructions which, when executed by the processor, cause the processor to:
receive the inlet relative humidity;
receive the inlet temperature;
receive the outlet relative humidity;
receive the outlet temperature;
calculate an inlet vapor density of influent air for the at least one room based on the inlet relative humidity and the inlet temperature; and
calculate an outlet vapor density of effluent air for the at least one room based on the outlet relative humidity and the outlet temperature.

3. The sensor station system of claim 2, wherein the electronic instructions further comprise calculating a moisture content of a product in the at least one room based on the inlet vapor density and the outlet vapor density.

4. The sensor station system of claim 1, wherein the computing device is configured to calculate the water balance of the at least one room over a duration of time.

5. The sensor station system of claim 1, further comprising:
a weight sensor configured to measure a first weight of a product positioned in the at least one room; and
a water activity sensor configured to measure a water activity of the product positioned in the at least one room.

6. The sensor station system of claim 5, wherein the computing device comprises a processor and a memory device in electronic communication with the processor, the memory including electronic instructions which, when executed by the processor, cause the processor to:
receive the inlet relative humidity;
receive the inlet temperature;
receive the outlet relative humidity;
receive the outlet temperature;
receive the first weight of the product;
receive the water activity of the product;
calculate a water loss of the product over a duration of time based on the inlet relative humidity, the inlet temperature, the outlet relative humidity, and the outlet temperature.

7. The sensor station system of claim 6, wherein the electronic instructions comprise calculating a second weight of the product after the duration of time based on the first weight, the water activity, and the water loss.

8. A computing device, comprising:
a processor;
a set of sensors in electronic communication with the processor, each sensor of the set of sensors being positioned at an air inlet or an air outlet of a chamber structure;
a memory device in electronic communication with the processor, the memory device including electronic instructions which, when executed by the processor, cause the processor to:
receive a set of sensor measurements from the set of sensors;
track an inlet vapor density at an inlet of the chamber structure;
track an outlet vapor density at an outlet of the chamber structure;
determine a water balance over time in the chamber structure based on the inlet vapor density and the outlet vapor density;
determine that a product is ready for removal from the chamber structure based on the water balance reaching a threshold amount; and
provide a signal to remove the product from the chamber structure.

9. The computing device of claim 8, wherein the set of sensors include:
an inlet relative humidity sensor to measure an inlet relative humidity at the air inlet of the chamber structure;
an inlet temperature sensor to measure an inlet temperature at the air inlet;
an outlet relative humidity sensor to measure an outlet relative humidity at the air outlet of the chamber structure; and
an outlet temperature sensor to measure an outlet temperature at the air outlet.

10. The computing device of claim 8, wherein the set of sensor measurements includes a temperature of the product, a dry bulb temperature, and a relative humidity.

11. The computing device of claim 8, wherein the set of sensor measurements comprises an electrical permittivity of the product and an electrical conductivity of the product.

12. The computing device of claim 8, wherein the inlet is a fixed inlet on the chamber structure and the outlet is a fixed outlet on the chamber structure.

13. The computing device of claim 8, wherein the set of sensor measurements includes a first weight of the product and a water activity of the product, and wherein the instructions further cause the processor to determine a final weight of the product based on the first weight, the water activity, and the water balance upon reaching the threshold amount.

14. The computing device of claim 8, wherein the water balance is configured to change over time based on the product drying in the chamber structure.

15. A sensor station network, comprising:
a set of rooms, each room of the set of rooms having an entrance location and an exit location;
a set of sensors positioned in each room of the set of rooms, wherein each room of the set of rooms includes an entrance relative humidity sensor and an entrance temperature sensor at the entrance location and an exit relative humidity sensor and an exit temperature sensor at the exit location; and
a computing device electrically connected to the set of sensors and to configured to calculate an air inflow vapor density for each of the entrance locations and an air outflow vapor density for each of the exit locations.

16. The sensor station network of claim 15, further comprising at least one intermediate node to relay sensor data from a set of sensors of at least one room to the computing device.

17. The sensor station network of claim 15, wherein the computing device is configured to calculate a water balance of at least one room of the set of rooms.

18. The sensor station network of claim 17, wherein the computing device is configured to calculate a moisture content value of a product in the at least one room based on the water balance.

19. The sensor station network of claim 18, wherein the computing device is configured to determine a weight of the product in the at least one room based on the water balance and the moisture content value.

20. The sensor station network of claim 15, further comprising a user device in electronic communication with the computing device and configured to output analytics and alerts based on at least one of the air inflow vapor densities and at least one of the air outflow vapor densities.

* * * * *